US00PP37196P2

(12) United States Plant Patent
Bergman

(10) Patent No.: US PP37,196 P2
(45) Date of Patent: Jan. 6, 2026

(54) ***LANTANA* PLANT NAMED 'LANZ0048'**

(50) Latin Name: ***Lantana camara* L.**
Varietal Denomination: LANZ0048

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/246,753

(22) Filed: Jun. 24, 2025

(51) Int. Cl.
*A01H 5/02* (2018.01)
*A01H 6/86* (2018.01)

(52) U.S. Cl.
USPC ..... Plt./227
CPC ..... *A01H 6/86* (2018.05)

(58) Field of Classification Search
USPC ..... Plt./227
CPC ..... A01H 5/02
See application file for complete search history.

*Primary Examiner* — Kent L Bell
(74) *Attorney, Agent, or Firm* — Dale Skalla

(57) ABSTRACT

A new *Lantana* plant named 'LANZ0048' having light yellow and pink umbels, where newly opened flowers are light yellow, and mature flowers are pink, excellent flower production, large plant growth and uniform dense semi-spreading habit with medium sized dark green foliage.

1 Drawing Sheet

Latin name of the genus and species of the plant claimed: *Lantana camara* L.
Varietal denomination: 'LANZ0048'.

BACKGROUND OF THE NEW PLANT

The present invention comprises a new *Lantana*, botanically known as *Lantana camara* L., and hereinafter referred to by the variety name 'LANZ0048'.

'LANZ0048' is a product of a planned breeding program in Gilroy, California. The new cultivar 'LANZ0048' has light yellow and pink umbels, where newly opened flowers are light yellow, and mature flowers are pink, excellent flower production, large plant growth and uniform dense semi-spreading habit with medium sized dark green foliage.

The new *Lantana* cultivar, 'LANZ0048', is the result of cross-pollination made in Gilroy, California in the summer of 2019. The female parent of the new cultivar is 'Bant Pin09', U.S. Plant Pat. No. 20,555, characterized by its purple/pink flower color and compact rounded growth habit. 'LANZ0048' differs from 'Bant Pin09' having smaller flowers, no seed set, and much larger plant size. The male parent of the new cultivar is the commercially available variety 'Havana Full Moon', having white flowers, an overall smaller plant size, and considerably more seed set than 'LANZ0048'.

The resulting seed was sown in February 2020, in a controlled greenhouse environment in Gilroy, California, and 'LANZ0048' was selected as one flowering plant within the progeny of the stated cross in May of 2020.

The first act of asexual reproduction of 'LANZ0048' was accomplished when vegetative stem cuttings were propagated from the initial selection in July 2020 in Gilroy, California.

BRIEF SUMMARY OF INVENTION

Horticultural examination of plants grown from cuttings of the plant initiated in July 2020, in Gilroy, California, and continuing thereafter, has demonstrated that the combination of characteristics as herein disclosed for 'LANZ0048' are firmly fixed and are retained through successive generations of asexual reproduction.

'LANZ0048' has not been observed under all possible environmental conditions. The phenotype may vary significantly with variations in environment such as temperature, light intensity, and day length.

A Plant Breeder's Right for this cultivar has not yet been applied for. 'LANZ0048' has not been made publicly available prior to the effective filing date of this application, notwithstanding any disclosure that may have been made less than one year prior to the effective filing date of this application by the inventor or another who obtained 'LANZ0048' directly from the inventor.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawings show typical flower and foliage characteristics of 'LANZ0048' with colors being as true as possible with illustrations of this type.

Figure 1:
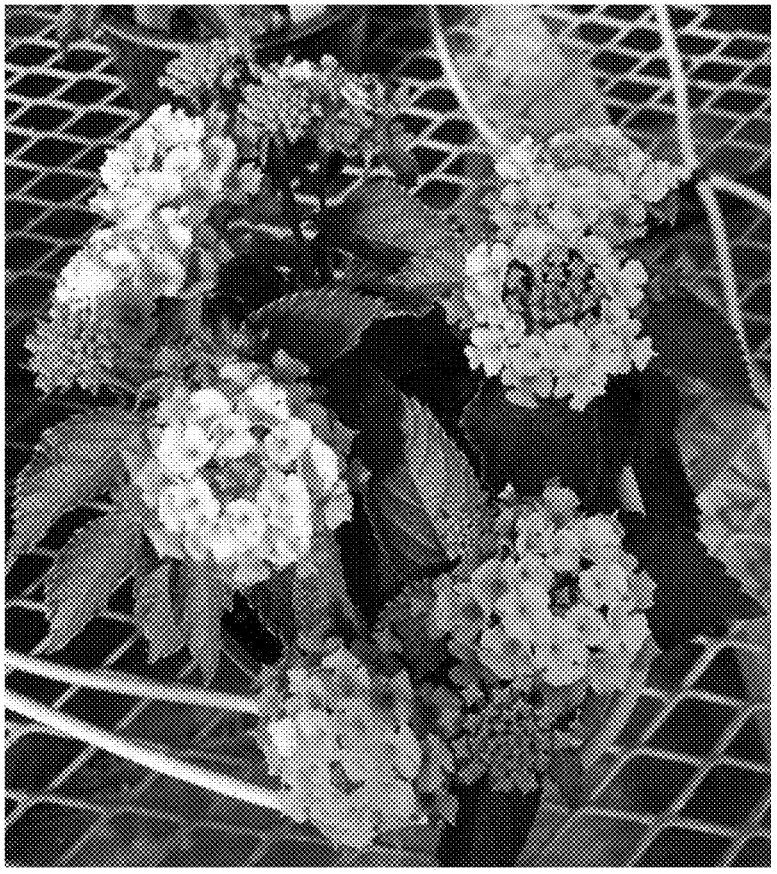
Figure 2:
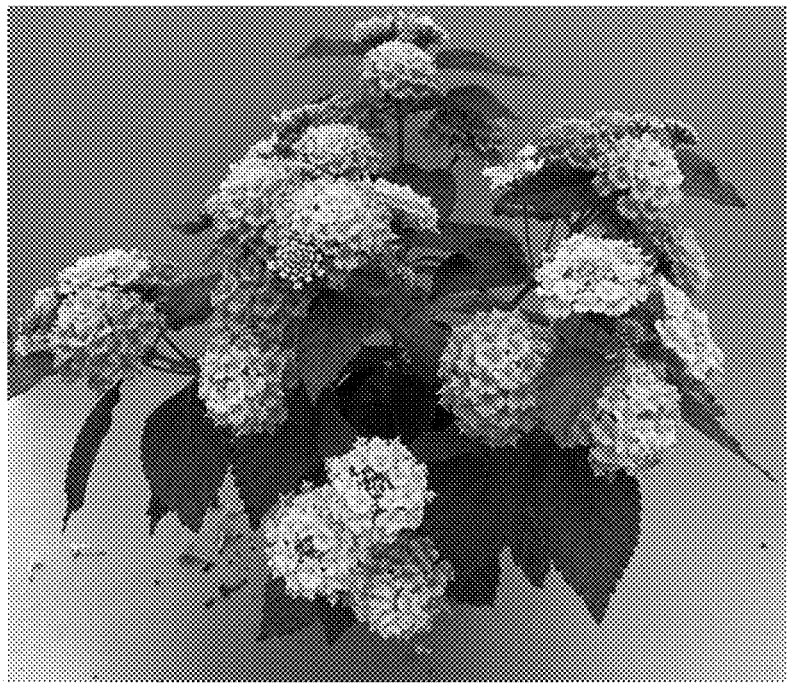

The photographic drawings show in FIG. 1 a close view of inflorescences taken in Gilroy, California in October 2020, and in FIG. 2 a whole flowering plant, approximately 3.5 months of age, taken in Andijk, The Netherlands in April 2023.

DETAILED BOTANICAL DESCRIPTION

The plant descriptions and measurements were taken in Gilroy, California May 2025. The plants were approximately 5 months old and were growing in 14-inch pots, three plants per pot, in a greenhouse.

Color references are made to The Royal Horticultural Society Colour Chart (R.H.S.) 2015.

TABLE 1

DIFFERENCES BETWEEN THE NEW VARIETY 'LANZ0048' AND A MOST SIMILAR VARIETY

| Traits | 'LANZ0048' | 'LANZ0008', U.S. Plant Pat. No. 28,175 |
|---|---|---|
| Seed set: | None observed | Moderate seed set |
| Internode length: | Shorter | Longer |
| Plant habit: | Semi-spreading | Spreading |

Plant:

*Form, growth and habit*.—Semi-woody, grown as an annual or perennial; vigorous semi-spreading habit; very well branched.

*Plant height*.—30 cm.

*Plant height* (*inflorescence included*).—32 cm.

*Plant width*.—66 cm.

Foliage:

*Type*.—Opposite.

*Immature, leaf color, upper surface*.—Closest to RHS137A.

*Lower surface*.—Closest to RHS 137C.

*Mature, leaf color, upper surface*.—RHS 139A.

*Lower surface*.—Closest to RHS 137B.

*Length*.—3.0-7.5 cm.

*Width*.—1.5-4.5 cm.

*Shape*.—Ovate.

*Base shape*.—Rounded.

*Apex shape*.—Acute.

*Margin*.—Serrate.

*Texture, upper*.—Hairy.

*Texture, lower surface*.—Hairy.

*Pattern of veining*.—Pinnate.

*Petioles color*.—RHS 144C.

*Petioles length*.—0.5-2.0 cm.

*Diameter of petiole*.—0.1-0.2 cm.

*Texture* (*upper and lower surface*).—Very short hairs.

Stem:

*Color of stem*.—RHS 146D.

*Length of stem*.—20.0-30.0 cm.

*Diameter*.—0.3 cm.

*Length of internodes*.—2.5-3.0 cm.

*Texture*.—Some hairs.

Inflorescence:

*Type*.—Umbel like, flattened semi-sphere the florets are sessile on an ovate receptacle.

*Blooming habit*.—Flowers continuously from spring through fall.

*Number of open flowers per inflorescence*.—About 38.

*Quantity of inflorescences per plant*.—20-35.

*Lastingness of individual blooms on the plant*.—About 3 weeks (depending on temperatures).

*Fragrance*.—Slightly spicy lemon.

*Umbel horizontal diameter*.—3.0-4.2 cm.

*Umbel vertical height*.—2.0-2.3 cm.

*Peduncle color*.—RHS 138A.

*Length of peduncle*.—1.0-4.0 cm.

*Peduncle diameter*.—0.2 cm.

*Texture*.—Some hairs.

Flower:

*Floret form*.—Corolla salver-shaped to shallow cup-shaped, with a relatively long tube at the base; each flower subtended by a single bract.

*Length of floret*.—1.5-2.0 cm.

*Width of floret*.—1.0 cm.

*Depth of floret*.—1.0 cm.

*Young floret, color upper surface*.—RHS 6B with shades of RHS 155A and RHS N155C.

*Young floret, color lower surface*.—RHS 155B blended with RHS N155B.

*Mid age floret, color upper surface*.—RHS 155A and/or RHS 56A with RHS 6B and/or RHS 55B surrounding throat.

*Mid age floret, color lower surface*.—RHS 155B and RHS 55D.

*Mature florets, color upper surface*.—RHS 154C and RHS 55D.

*Mature floret, color lower surface*.—RHS 155B and RHS 55D with RHS 55A and RHS 6B surrounding throat.

*Apex shape*.—Rounded.

*Degree of lobation*.—Moderate.

*Margin*.—Entire.

*Base*.—Fused.

*Texture, upper surface*.—Smooth.

*Lower surface*.—Smooth.

*Tube, color outer surface*.—RHS 155A and RHS N155B and RHS 56A.

*Tube, color inner surface*.—RHS 155A and RHS 36D and RHS 6B.

*Tube, length*.—1.0 cm.

*Tube, diameter* (*at opening*).—0.1 cm.

*Tube, texture outer surface*.—Smooth.

*Inner surface*.—Very small hairs.

Bud (just before opening):

*Color*.—RHS 4D with a blush of RHS 56C.

*Length*.—0.8-1.0 cm.

*Width*.—0.2 cm at the apex.

*Shape*.—Tubular with a flared apex.

Bract:

*Color upper and lower*.—Closest to RHS 143B.

*Shape*.—Linear.

*Apex*.—Acute.

*Base*.—Linear, stipulate.

*Margin*.—Entire.

*Length*.—0.5-0.8 cm.

*Diameter*.—0.15 cm.

*Texture, upper surface*.—Small hairs.

*Lower surface*.—Small hairs.

Calyx:

*Number of sepals*.—5, fused sepals forming a short tube around the base of the floret.

*Shape*.—Tubular.

*Color of sepals upper and lower*.—RHS 145C.

*Length of sepals*.—0.3 cm.

*Width of sepals*.—0.15 cm.

*Apex shape*.—Obtuse.

*Apex margins*.—Entire.

*Texture, outer surface*.—Small hairs.

*Inner surface*.—Smooth.

Reproductive organs:

Gynoecium:

*Pistil quantity*.—One.

*Length*.—0.4-0.5 cm.

*Style color*.—RHS 150D.
*Style length*.—0.3 cm.
*Stigma color*.—RHS 144C.
*Ovary color*.—RHS 145B.
*Ovary length*.—0.1 cm.
*Ovary diameter*.—0.1 cm.

Androecium:

*Stamen quantity*.—4.
*Color of filaments*.—RHS 158C.
*Length filaments*.—0.05 cm.
*Anther color*.—RHS 4C.
*Length of anthers*.—0.1 cm.
*Color of pollen*.—RHS 4D.
*Pollen amount*.—Scant.
*Fertility/seed set*.—Very low. No seed set has been observed.
*Disease/pest resistance*.—No significant disease or pest infestations have been identified or observed.

What is claimed is:

1. A new and distinct variety of *Lantana* plant named 'LANZ0048' substantially as illustrated and described herein.

* * * * *